United States Patent
Martini et al.

(10) Patent No.: US 11,313,800 B2
(45) Date of Patent: Apr. 26, 2022

(54) METHOD FOR DETECTING AND QUANTIFYING ADDITIVES USED IN THE ENHANCED RECOVERY OF OIL AND SHALE GAS

(71) Applicants: TOTAL SA, Courbevoie (FR); UNIVERSITE CLAUDE BERNARD LYON 1, Villeurbanne (FR); CENTRE NATIONAL DE LA RECHERCHE SCIENTIFIQUE—CNRS, Paris (FR)

(72) Inventors: Mattéo Martini, Villars les Dombes (FR); Olivier Tillement, Fontaines Saint Martin (FR); Arthur Marais, Lochrist (FR); Christian Hurtevent, Saint Chamarand (FR); Stéphane Jouenne, Bizanos (FR)

(73) Assignees: TOTAL SA, Courbevoie (FR); UNIVERSITE CLAUDE BERNARD LYON 1, Villeurbanne (FR); CENTRE NATIONAL DE LA RECHERCHE SCIENTIFIQUE, Paris (FR)

(*) Notice: Subject to any disclaimer, the term of this patent is extended or adjusted under 35 U.S.C. 154(b) by 617 days.

(21) Appl. No.: 16/088,232

(22) PCT Filed: Apr. 20, 2016

(86) PCT No.: PCT/FR2016/050912
§ 371 (c)(1),
(2) Date: Sep. 25, 2018

(87) PCT Pub. No.: WO2017/182720
PCT Pub. Date: Oct. 26, 2017

(65) Prior Publication Data
US 2019/0204223 A1    Jul. 4, 2019

(51) Int. Cl.
*G01N 21/00*  (2006.01)
*G01N 21/64*  (2006.01)
*G01N 33/28*  (2006.01)
*C08G 69/24*  (2006.01)
*G01N 21/85*  (2006.01)
*C09K 8/588*  (2006.01)

(52) U.S. Cl.
CPC .......... *G01N 21/643* (2013.01); *C08G 69/24* (2013.01); *G01N 21/6408* (2013.01); *G01N 21/85* (2013.01); *G01N 33/2823* (2013.01); *C09K 8/588* (2013.01)

(58) Field of Classification Search
CPC .................................................... G01N 21/643
USPC ......................................................... 436/172
See application file for complete search history.

(56) References Cited

FOREIGN PATENT DOCUMENTS

WO    2011/055038 A1    5/2011
WO    2015/075299 A1    5/2015

OTHER PUBLICATIONS

Farooqui et al. "The Effect of Molecular Weight Distribution on the Inhibition Efficiency Performance of Polymeric Scale Inhibitors during Retention." Paper presented at the CORROSION 2015, Dallas, Texas, Mar. 2015. (Year: 2015).*

(Continued)

*Primary Examiner* — Christine T Mui
*Assistant Examiner* — Emily R. Berkeley
(74) *Attorney, Agent, or Firm* — Oliff PLC

(57) ABSTRACT

A method for the detection and quantification, in a complex aqueous fluid, of additives and water-soluble polymers used in the enhanced recovery of oil and shale gas.

11 Claims, 2 Drawing Sheets

(56) References Cited

OTHER PUBLICATIONS

Apr. 29, 2020 Office Action issued in European Application No. 16 724 440.9.
Jul. 7, 2016 International Search Report issued in International Patent Application No. PCT/FR2016/050912.
Dickson Gudgin, Eva F. et al., "Ultrasensitive Bioanalytical Assays Using Time-Resolved Fluorescence Detection", Pharmac. Ther., vol. 66, pp. 207-235, (1995).
Wever, D. A. Z. et al., "Polymers for Enhanced Oil Recovery: A Paradigm for Structure-Property Relationship in Aqueous Solution", Progress in Polymer Science, vol. 36, pp. 1558-1628, (May 27, 2011).
Armelao, L. et al., "Design of Luminescent Lanthanide Complexes: From Molecules to Highly Efficient Photo-Emitting Materials", Coordination Chemistry Reviews, vol. 254, pp. 487-505, (2010).
Brichart, Thomas, "Traceurs Fluorescents À Base De Lanthanides En Milieu Complexe", HAL Archives-Ouvertes, (2014).
Brichart, Thomas et al., "The Use of Fluorescent Tracers for Inhibitor Concentration Monitoring Useful for Scale Inhibitor Squeeze Evaluation", IPTC-17933-MS, (2014).
Horrocks, W. D. et al., "Lanthanide Ion Probes of Structure in Biology. Laser-Induced Luminescence Decay Constants Provide a Direct Measure of the Number of Metal-Coordinated Water Molecules", Journal of the American Chemical Society, vol. 101:2, pp. 334-340, (Jan. 17, 1979).

\* cited by examiner

METHOD FOR DETECTING AND QUANTIFYING ADDITIVES USED IN THE ENHANCED RECOVERY OF OIL AND SHALE GAS

TECHNICAL FIELD

The present invention relates to a method for detecting and quantifying additives used in the enhanced recovery of oil and shale gas, in a complex aqueous fluid. In particular, the present invention relates to a method for detecting and quantifying water-soluble polymers used in the enhanced recovery of oil and shale gas, in a complex aqueous fluid.

BACKGROUND OF THE INVENTION

It is well known in the oil exploitation of a deposit that generally no more than half, or even less, of the oil originally present in the deposit is extracted, and that it is necessary to use several advanced recovery techniques to maximize the proportion of oil extracted.

Recovery by primary means, i.e. utilization of the extraction energy resulting from gases or liquids present underground under the effect of a certain pressure in the deposit, only allows small percentages of the total oil present in the deposit to be extracted.

After this primary recovery, another recovery technique is employed: enhanced oil recovery. Several wells are drilled in the reservoir: injection wells and production wells. In most cases water is injected into the reservoir via the injection wells. This has the effect of maintaining the pressure difference with the surface and thus ensuring the flow of oil in the reservoir, the oil being displaced by the water that is injected. However, the mobility of the water is often greater than that of the oil, which generates unstable fronts between the two immiscible liquids and phenomena of viscous fingering. As a result, the scavenging efficiency at the macroscopic scale remains low, a large part of the deposit is not scavenged by the injected water and a significant quantity of oil remains in the reservoir. Increasing the viscosity of the liquid that is injected makes it possible to reduce the mobility ratio between the liquid injected and the oil and increase the scavenging efficiency at the macroscopic scale. Thus, additives are added to the injected water to increase its viscosity. By making the water less mobile, better control of mobility between the liquid injected and the oil can be obtained.

Among the additives used, the water-soluble polymers that make it possible to increase the viscosity of water can be mentioned, such as polyacrylamides or xanthan. These polymers have a high molecular weight, typically comprised between 1 and 30 MDa, in order to increase the viscosity of water at least cost. The polymers used in the enhanced recovery of oil and shale gas are therefore different from the polymers used as deposition or corrosion inhibitors, which have lower molecular weights. They are generally used in the form of aqueous solutions and are in particular described in the journal "Polymers for enhanced oil recovery: A paradigm for structure-property relationship in aqueous solution", Progress in Polymer Science, Vol. 36, pp. 1558-1628, 2011.

However, the conditions in wellbores and reservoirs are such that they could cause degradation of the additives used in the enhanced recovery of oil and shale gas, which results in a loss of efficiency. The degradation of the additives can be estimated by measuring the viscosity of the solution and the concentration of additives. Thus, it is useful to be able to determine (detect and/or quantify) these additives at the level of the injection and production wells in order to determine their level of degradation. This makes it possible to estimate the degradation of the additives and, if necessary, inject an additional quantity of additives, adjusted to take account of the economic constraints of the method and of its environmental impact and optimize the enhanced recovery of oil and shale gas.

The methods used at present for determining the additives used in the enhanced recovery of oil and shale gas are often imprecise and/or take a long time and require equipment that is often insufficiently adapted to the exploitation conditions.

Moreover, the development of a quick and reliable method of detection is made difficult by the presence of a variety of compounds such as salts and organic residues in the fluid constituting the exploitation water. Owing to the presence of these compounds, the complex fluid produced in particular presents intrinsic fluorescence that prevents the detection of these additives, optionally labelled with a fluorescent probe, using conventional fluorescence techniques. Finally, the production sites are generally located in remote places, far from the local analytical laboratories, which is an additional constraint.

It would therefore be desirable to be able to determine the additives used in the enhanced recovery of oil and shale gas directly on site, in the injection or production water, using a method that is simple, reliable and accurate, usable for a variety of additives and that can be implemented using compact equipment that can be moved easily.

The inventors demonstrated that these requirements could be satisfied by mixing the fluids to be analysed, which can contain additives used in the enhanced recovery of oil and shale gas, with a detecting solution comprising at least one lanthanide ion and optionally at least one chelating agent of the lanthanide ion, and using the time-resolved fluorescence method. This method in fact makes it possible to ignore the natural fluorescence of the exploitation water, which has very short emission times, and only collect the light emitted after a delay from a few microseconds to a millisecond, preferably from 100 microseconds to a millisecond, resulting from the fluorescence of the additives used in enhanced oil recovery that are labelled in this way. Moreover, the possible pre-complexing of the lanthanide ions with a chelating agent makes it possible to improve the sensitivity of detection of the additives used in enhanced oil recovery, even despite the increase in fluorescence of the lanthanide ions associated with the presence of the chelating agent. The present method also makes it possible to detect additives used in enhanced oil recovery at low complexing power or easily excitable in the near UV/visible.

Moreover, this method has the advantage of specifically identifying the type of additive used in enhanced oil recovery, without a prior labelling step and even when it is present in a complex fluid formed by the production water in the oil or shale gas medium, as a function of its optical signature, simultaneously exploiting the excitation and emission spectra and the lifetimes of the signals emitted.

SUMMARY OF THE INVENTION

The present invention relates to a method for detecting additives used in the enhanced recovery of oil and shale gas, in injection water or production water, said method comprising:
a. mixing a detecting solution comprising at least one lanthanide cation and optionally a chelating agent of the lanthanides, with a sample of injection water or of production water to be analysed comprising at least one additive used in the enhanced recovery of oil and shale gas, under conditions allowing complexing of the lanthanide by the additive present, b. detecting and, if appropriate, quantifying the variation in fluorescence associated with the presence of the additive in the injection water or the production water by time-resolved fluorescence.

DETAILED DESCRIPTION OF EMBODIMENTS

Definitions

By "a $C_x$ to $C_y$ alkyl group" is meant, within the meaning of the present invention and in the following text, a linear or branched alkyl chain, or a cycloalkyl, having x to y carbon atoms.

By "a $C_1$ to $C_4$ alkyl group" is meant, within the meaning of the present invention and in the following text, a linear or branched alkyl chain, or a cycloalkyl, having 1 to 4 carbon atoms. For example, the following linear alkyl chains: methyl, ethyl, n-propyl and n-butyl. As examples of a branched alkyl chain, we can mention the following groups: iso-propyl, isobutyl, sec-butyl and tert-butyl can be mentioned.

By "a $C_1$ to $C_{10}$ alkyl group" is meant, within the meaning of the present invention and in the following text, a linear or branched alkyl chain, or a cycloalkyl, having 1 to 10 carbon atoms. For example, the following linear alkyl chains: methyl, ethyl, n-propyl, n-butyl, n-pentyl, n-hexyl, n-heptyl, n-octyl, n-nonyl and n-decyl can be mentioned. As examples of a branched alkyl chain, the above groups and the following groups: isopentyl, 2,2-dimethylpropyl, iso-octyl, iso-nonyl and iso-decyl can be mentioned.

By "substituted or unsubstituted" is meant, within the meaning of the present invention and in the following text, that the alkyl or aryl group can be substituted with one or more functional groups, for example selected from the amine, imine, nitro, cyano, amide, imide, hydroxyl, alkoxy, carbonyl, carboxyl, ester, thiol, thioether, thioester and halide groups.

Detecting Solution for Carrying Out the Method for Detecting Additives

Application of the detection method comprises the use of a detecting solution comprising at least one lanthanide cation and optionally at least one chelating agent of the lanthanides.

The lanthanide cation usable in the detecting solution can be selected from the elements from atomic number 57 (lanthanum) to 71 (lutetium), such as Pr, Nd, Sm, Eu, Tb, Dy, Ho, Er, Tm and Yb, as well as mixtures thereof. The present method is particularly suitable for a detecting solution comprising europium. Advantageously, measurement of the fluorescence emitted by europium can be carried out through disposable plastic cells, without the need to use cells transparent in the UV (such as quartz or silica cells).

In a specific embodiment, the detecting solution further comprises at least 1 g/L of chloride ions, and preferably a concentration of chloride ions between 5 and 50 g/L.

In another particular embodiment that can be combined with the preceding embodiments, the detecting solution further comprises at least 1 g/L of a compound with strong buffer capacity, used in the production of buffer solution, and allowing the pH value to be maintained after adding 1/10 of water to be analysed in a pH range below 0.5 unit, for example 4-(2-hydroxyethyl)-1-piperazine-ethanesulphonic acid (HEPES) or also sodium acetate.

The detecting solution optionally comprises a chelating agent of the lanthanides. By "chelating agent of the lanthanides" is meant an ion or a molecule bearing chemical functions allowing it to bind to one or more central atoms or ions of said lanthanide and the lanthanide/ligand interaction thus formed is greater than the lanthanide/water interaction and preferably greater than the lanthanide/chloride interaction, thus allowing pre-complexing of the lanthanide ions, reducing the number of water molecules present in the coordination sphere of the lanthanide, resulting in a decrease of the quenching effect of the water on the fluorescence of the lanthanide ion (DeW. Horrocks et al., JACS 1979 101:2, 334-340).

Preferably, the chelating agents of the lanthanides usable in the detecting solution are selected from:
(i) molecules comprising at least one amine function, preferably two amine functions, and/or
(ii) molecules comprising at least one carboxylic acid function, in particular maleic acid or the polymeric derivatives of maleic acid.

In a specific embodiment, the chelating agent further comprises at least one aryl group, preferably a single heterocyclic group, substituted or unsubstituted, for example a pyridine group and substituted derivatives thereof. Besides the chelating effect supplied by the amine function or carboxylic acid, the presence of an aryl group and for example a pyridine group in addition makes it possible to amplify the fluorescence signal by an antenna effect (Armelao, L. et al. COORDINATION CHEMISTRY REVIEWS Volume: 254 Issues: 5-6 Special Issue: SI Pages: 487-505 Published: March 2010).

In a preferred embodiment, the chelating agent is selected from diaminopyridine, imidazoline, hydrolysed polymaleic anhydride, polycarboxylic acids, EDTA, oxalic acid, acetylacetonate, thiodiacetate, nitrilotriacetic acid (NTA), derivatives thereof or mixtures thereof.

The ratio of the concentration by weight of chelating agent to lanthanide in the detecting solution is between 1:10 and 10:1, for example between 1:3 and 3:1.

The invention relates in particular to a detecting solution for detecting additives used in the enhanced recovery of oil and shale gas, comprising:
i. a lanthanide cation, for example Eu3+,
ii. chloride ions at more than 1 g/L;
iii. if appropriate, a chelating agent of the lanthanides, for example selected from diaminopyridine, imidazoline, hydrolysed polymaleic anhydride, polycarboxylic acids, oxalic acid, acetylacetonate, thiodiacetate, or derivatives thereof, EDTA, nitrilotriacetic acid (NTA);
iv. if appropriate, a chemical compound used conventionally in the production of buffer solutions, for example 4-(2-hydroxyethyl)-1-piperazine-ethanesulphonic acid (HEPES) at more than 1 g/L;
if appropriate, the ratio of the concentration of chelating agent to lanthanide being between 1:10 and 10:1, preferably between 1:3 and 3:1.

In a particular embodiment, the detecting solution comprises between 1 and 10 000 ppm of lanthanide cations, in particular originating from $EuCl_3.6H_2O$, 10 and 5000 ppm of 2,5-diaminopyridine and between 1 and 50 g/L of NaCl, at a pH between 4 and 8.

The present invention relates to the detecting solutions as defined above for the use thereof in a method for detecting additives used in the enhanced recovery of oil and shale gas as defined below.

Aqueous Fluid to be Analysed, Extraction and Mixing with the Detecting Solution

The method for detecting additives used in the enhanced recovery of oil and shale gas comprises extraction of a sample (aqueous fluid) to be analysed and mixing it with the detecting solution defined above.

Preferably, the aim of the method is the detection of additives used in the enhanced recovery of oil and shale gas, in particular in an extract of a petroleum fluid containing water, for example an extract from a well producing oil or shale gas. In a preferred embodiment of the method according to the invention, a sample of aqueous fluid to be analysed is extracted from a well producing oil or shale gas or from industrial water collected during the process of exploitation and/or manufacture.

Preferably, the additive used in the enhanced recovery of oil and shale gas is contained in the aqueous fluid at a concentration less than or equal to 500 ppm, preferably less than or equal to 10 ppm, even more preferably less than or equal to 1 ppm, for example between 100 ppb and 500 ppm, or between 100 ppb and 10 ppm or also between 10 ppb and 1 ppm.

In the method according to the invention, the volume extracted from the sample to be analysed (for example extracted from an oil or shale gas well) can be for example between 0.1 mL and 1 litre, 5 litres, 10 litres or more.

The volume extracted can be treated before analysis, for example by acid/base/oxidation/precipitation or by steps of filtration or sedimentation in order to remove certain undesirable compounds, before mixing with the detecting solution.

This sample (for example extracted from an oil or shale gas well) is mixed with the detecting solution, for example in proportions from 1:100 to 100:1 v/v between the volume of the sample to be analysed and the volume of detecting solution and preferably between 1:20 and 1:5, for example around 1:10.

In a particular embodiment, the lanthanide ions pre-complexed with the chelating agents present in the detecting solution form complexes with the additive used in the enhanced recovery of oil and shale gas optionally present in the sample. This results in a decrease in the quenching effect of the water molecules around the lanthanide cations and therefore an increase in the fluorescence of the lanthanide cations.

Additives Used in the Enhanced Recovery of Oil and Shale Gas

In an embodiment, the additive used in the enhanced recovery of oil and shale gas does not have intrinsic fluorescence. Advantageously, with the method according to the present invention, the additive to be detected has not been coupled to a chelating agent before it is injected or to a luminescent agent or some other labelling agent.

The additives used in the enhanced recovery of oil and shale gas that can be present in the sample to be analysed, and detectable by the detection method according to the invention, are in particular polymers, preferably water-soluble polymers. By "polymers" is meant synthetic polymers and biopolymers (polymers originating from biomass).

The polymers used in the enhanced recovery of oil and shale gas can be linear, star or comb polymers.

They can be polymers comprising a single repeat unit (homopolymers) or several repeat units (copolymers), for example two repeat units (bipolymers), three repeat units (terpolymers), four repeat units or more.

The polymers comprising several repeat units can be block copolymers, random copolymers or alternating copolymers. They can also be graft copolymers.

Advantageously, the polymer used in the enhanced recovery of oil and shale gas is a linear random copolymer.

In an embodiment of the invention, the polymer is a non-ionic, anionic or zwitterionic polymer, preferably anionic.

Preferably, the polymer used in the enhanced recovery of oil and shale gas is a polymer comprising at least one repeat unit comprising an amide bond.

The additive used in the enhanced recovery of oil and shale gas can be selected from:
- polymers comprising at least one repeat unit comprising an amide bond;
- anionic biopolymers such as xanthan;
- cationic polymers, such as polymers based on diallyldimethylammonium chloride (polyDADMACs).

Advantageously, the polymer comprising at least one repeat unit comprising an amide bond comprises a repeat unit of formula I

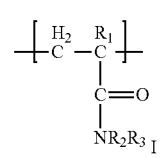

where $R_1$ is —H or —$CH_3$, $R_2$ is —H or a substituted or unsubstituted $C_1$ to $C_4$ alkyl group, $R_3$ is —H or a substituted or unsubstituted $C_1$ to $C_4$ alkyl group, or an -L-$R_4$ group, where L is a bond or a substituted or unsubstituted $C_1$ to $C_{10}$ alkyl group, interrupted by 0, 1 or more —$NR_2$— or —O— or —S— bonds, or a -(substituted or unsubstituted $C_1$ to $C_{10}$ alkyl)-($N^+R_6R_7$)-(substituted or unsubstituted $C_1$ to $C_{10}$ alkyl)- group with $R_6$ and $R_7$ which are either —H or a substituted or unsubstituted $C_1$ to $C_4$ alkyl group, and $R_4$ is —H or a carboxylate group (—$COO^-$) or a sulphonate group (—$SO_3^-$), optionally with a counter-ion.

Preferably, the polymer comprising at least one repeat unit comprising an amide bond comprises a repeat unit of formula I where $R_1$ is —H or —$CH_3$, $R_2$ is —H or a substituted or unsubstituted $C_1$ to $C_4$ alkyl group, $R_3$ is —H or a substituted or unsubstituted $C_1$ to $C_4$ alkyl group, or an -L-$R_4$ group, where L is a bond or a substituted or unsubstituted $C_1$ to $C_{10}$ alkyl group, interrupted by 0, 1 or more —$NR_2$— or —O— or —S— bonds, and $R_4$ is —H or a carboxylate group (—$COO^-$) or a sulphonate group (—$SO_3^-$), optionally with a counter-ion.

Particularly preferably, the polymer comprising at least one repeat unit comprising an amide bond comprises a repeat unit of formula I where $R_1$ is —H, $R_2$ is —H, $R_3$ is —H or an -L-$R_4$ group, where L is a bond or a substituted or unsubstituted $C_1$ to $C_{10}$ alkyl group, interrupted by 0, 1 or more —$NR_2$— or —O— or —S— bonds, and $R_4$ is a sulphonate group (—$SO_3^-$) with a counter-ion.

When the $R_4$ group comprises a counter-ion, the latter is preferably selected from $H^+$, the cations of alkali metals and the primary, secondary and tertiary ammoniums. The counter-ion can also be selected from $Na^+$, $K^+$, $Li^+$, $NH_4^+$, $Zn^+$, $Ca^{2+}$, $Zn^{2+}$, $Al^{3+}$ and $Mg^{2+}$.

For example, the polymer comprises a repeat unit of formula I where $R_1$, $R_2$ and $R_3$ are —H or a repeat unit of formula I where $R_1$ and $R_2$ are —H and $R_3$ is -L-$R_4$ where L is a tert-butyl group and $R_4$ is a sulphonate group (—$SO_3^-$), with a counter-ion, preferably Na+.

In an embodiment of the invention, the polymer comprising at least one repeat unit of formula I further comprises a repeat unit of formula II

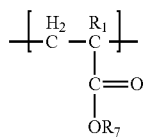

II where $R_1$ is —H or —$CH_3$, and $OR_7$ is O—H or $O^-$ and a counter-ion, said counter-ion preferably being selected from $H^+$, the cations of alkali metals and the primary, secondary and tertiary ammoniums. The counter-ion can also be selected from $Na^+$, $K^+$, $Li^+$, $NH_4^+$, $Zn^+$, $Ca^{2+}$, $Zn^{2+}$, $Al^{3+}$ and $Mg^{2+}$.

For example, the polymer is a copolymer comprising a repeat unit of formula I where $R_1$, $R_2$ and $R_3$ are —H and a repeat unit of formula II where $R_1$ is —H and $OR_7$ is $O^-Na^+$. This copolymer comprises at least 25 mol % of repeat unit of formula II, for example between 25 and 75 mol %.

In another particular embodiment that can be combined with the preceding embodiments, the polymer comprising a repeat unit of formula I further comprises a repeat unit of formula III

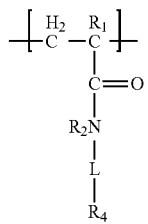

III where $R_1$ is —H or —$CH_3$, $R_2$ is —H or a substituted or unsubstituted $C_1$ to $C_4$ alkyl group, L is a bond or a substituted or unsubstituted $C_1$ to $C_{10}$ alkyl group, interrupted by 0, 1 or more —$NR_2$— or —O— or —S— bonds, or a -(substituted or unsubstituted $C_1$ to $C_{10}$ alkyl)-($N^+R_6R_7$)-(substituted or unsubstituted $C_1$ to $C_{10}$ alkyl)- group with $R_6$ and $R_7$ which are either —H or a substituted or unsubstituted $C_1$ to $C_4$ alkyl group, and $R_4$ is —H or a carboxylate group (—$COO^-$) or a sulphonate group (—$SO_3^-$), optionally with a counter-ion.

Preferably, the polymer comprising a repeat unit of formula I further comprises a repeat unit of formula III where $R_1$ is —H or —$CH_3$, $R_2$ is —H or a substituted or unsubstituted $C_1$ to $C_4$ alkyl group, $R_3$ is —H or a substituted or unsubstituted $C_1$ to $C_4$ alkyl group, or an -L-$R_4$ group, where L is a bond or a substituted or unsubstituted $C_1$ to $C_{10}$ alkyl group, interrupted by 0, 1 or more —$NR_2$— or —O— or —S— bonds, and $R_4$ is —H or a carboxylate group (—$COO^-$) or a sulphonate group (—$SO_3$), optionally with a counter-ion.

Particularly preferably, the polymer comprising a repeat unit of formula I further comprises a repeat unit of formula III where $R_1$ is —H, $R_2$ is —H, $R_3$ is —H or an -L-$R_4$ group, where L is a bond or a substituted or unsubstituted $C_1$ to $C_{10}$ alkyl group, interrupted by 0, 1 or more —$NR_2$— or —O— or —S— bonds, and $R_4$ is a sulphonate group (—$SO_3^-$) with a counter-ion.

For example, the polymer is a copolymer comprising a repeat unit of formula I where $R_1$, $R_2$ and $R_3$ are —H and a repeat unit of formula III where $R_1$ and $R_2$ are —H, L is a tert-butyl group and $R_4$ is a sulphonate group (—$SO_3^-$), with a counter-ion, preferably $Na^+$.

In another particular embodiment that can be combined with the preceding embodiments, the polymer comprising a repeat unit of formula I further comprises a repeat unit originating from the polymerization of a non-ionic monomer. Preferably said non-ionic monomer is selected from acryloyl morpholine, N-vinylcaprolactam, N-vinylpyrrolidone, N,N-dimethylacrylamide, N-isopropylacrylamide, diacetone acrylamide, N-vinylformamide, N-vinylacetamide, N-vinylpyridine, hydroxybutyl vinyl ether and isoprenol. Particularly preferably, the non-ionic monomer is N-vinylpyrrolidone.

For example, the polymer is a copolymer comprising a repeat unit of formula I where $R_1$, $R_2$ and $R_3$ are —H, a repeat unit of formula III where $R_1$ and $R_2$ are —H, L is a tert-butyl group and $R_4$ is a sulphonate group (—$SO_3$), with a counter-ion, preferably $Na^+$ and a repeat unit originating from the polymerization of N-vinylpyrrolidone.

In another particular embodiment that can be combined with the preceding embodiments, the polymer comprising a repeat unit of formula I further comprises a repeat unit comprising a hydrophobic group, i.e. non-polar, preferably of formula IV

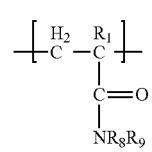

IV where $R_1$ is —H or —$CH_3$, $R_8$ and $R_9$ are independently a substituted or unsubstituted $C_7$ to $C_{20}$ alkyl group, a substituted or unsubstituted aryl group, a substituted or unsubstituted -aryl-($C_1$ to $C_{20}$ alkyl) group or a substituted or unsubstituted —($C_1$ to $C_{20}$ alkyl)-aryl group, where $R_8$ and/or $R_9$ are different from H.

Preferably, the repeat unit comprising a hydrophobic group is present in the copolymer between 0.01 and 5 mol %, yet more preferably between 0.1 and 1.5 mol %.

In another particular embodiment that can be combined with the preceding embodiments, the polymer does not comprise quaternary ammonium.

In another particular embodiment that can be combined with the preceding embodiments, the polymer is not a copolymer of acrylamidomethylpropane sulphonic acid (AMPS), of maleic acid and of acrylic acid.

In another particular embodiment that can be combined with the preceding embodiments, the polymer is not sulphonated polyphosphinocarboxylic acid.

In another particular embodiment that can be combined with the preceding embodiments, the polymer has a molecular weight greater than 100 kDa, preferably greater than 200 kDa, for example between 100 kDa and 30 Mda or between 1 MDa and 30 MDa.

Detection of the Additives in the Sample to be Analysed

For detecting the additives used in the enhanced recovery of oil and shale gas in the sample to be analysed with the method according to the invention, the variation in fluorescence between this mixture comprising lanthanide ions optionally complexed with an additive and a control mixture (for example not containing an additive or containing a known quantity of additive) is measured by time-resolved fluorescence.

Due to the decrease in the quenching effect of water on the lanthanide in the presence of the additive, the change in fluorescence with respect to a reference solution without the additive (or a known quantity of additive) is thus directly and specifically linked to the presence of the additives used in the enhanced recovery of oil and shale gas in the fluid to be analysed.

Comparison of the characteristics of emission, excitation and/or lifetime of the free lanthanide ions and of the complexed lanthanide ions thus makes it possible to detect and, if appropriate, quantify the additives used in the enhanced recovery of oil and shale gas present in the fluid extracted.

According to the invention, the additive used in the enhanced recovery of oil and shale gas is detected, and the level thereof is quantified, using a time-resolved fluorescence method, which is in particular described in the article "Ultrasensitive bioanalytical assays using time resolved fluorescence detection", Pharmacol. Ther. Vol. 66(2), pp. 207-35, 1995. The latter is based on the application of a delay, called integration delay, between the excitation of the sample to be analysed and the measurement of the signal emitted, so as to eliminate short-lived parasitic fluorescences. This method can be implemented at ambient temperature, in particular using apparatus of the Cary Eclipse type from the company Agilent.

The excitation wavelength can be comprised between 200 and 600 nm and the emission wavelength can be comprised between 300 and 800 nm. The integration delay can be comprised between 0.001 and 10 ms, preferably between 0.01 and 5 ms, more preferably between 0.1 and 3 ms. In certain cases, the longer this delay, the better the signal/noise ratio, which improves the reliability of measurement. The photon collection duration can range from 0.1 to 10 ms, for example.

This method can be applied in various ways. Thus, it is possible to compare the emission intensity of the sample tested with those obtained at different concentrations of additives used in the enhanced recovery of oil and shale gas, and deduce from that the concentration of additive in the sample. As a variant, it is possible to detect several additives used in the enhanced recovery of oil and shale gas in the sample tested by measuring the rate of decrease of the signal emitted by the sample, or half-life, and by comparing the values obtained with those known for the various additives to be detected.

FIGURES

Figure 1:
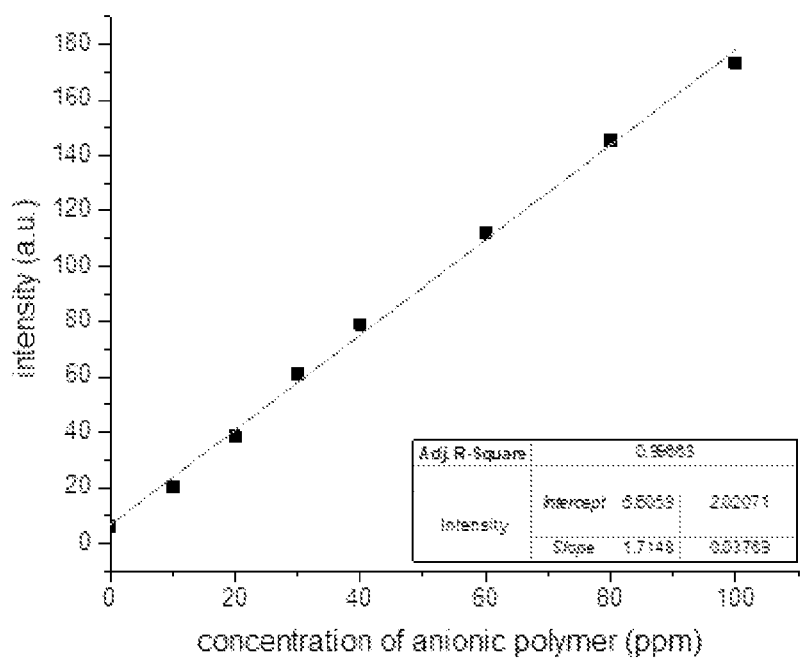
FIG. 1 shows the calibration curve of polymer 3630 with Eu-2,5-diaminopyridine according to Example 8.

The present invention will be better understood in light of the following non-limitative examples, which are given purely for purposes of illustration and do not aim to limit the scope of this invention, which is defined by the accompanying claims.

EXAMPLES

I—Preparation of the Detecting Solutions and of the Solutions of Polymers

Example 1

Preparation of a Concentrated Solution of Europium 200 mg of europium chloride hexahydrate ($EuCl_3.6H_2O$, CAS No. 13759-92-7) is weighed in a 100-mL flask and 100 mL of ultra-pure water is added. A solution of europium chloride hexahydrate at 2000 ppm is obtained.

Example 2

Preparation of a Concentrated Solution of 2,5-diaminopyridine 100 mg of 2,5-diaminopyridine dihydrochloride ($C_5H_7N_3$. 2HCl, CAS No. 26878-35-3) is weighed in a 100-mL flask and 100 mL of ultra-pure water is added. A solution of 2,5-diaminopyridine dihydrochloride at 1000 ppm is obtained.

Example 3

Preparation of a Concentrated Solution of HEPES (Buffer)

1.191 g of HEPES ($C_8H_{18}N_2O_4S$, CAS No. 7365-45-9) is weighed in a 100-mL flask and 100 mL of ultra-pure water is added. A solution of HEPES at 11 910 ppm is obtained.

Example 4

Preparation of a Detecting Solution 5 g of sodium chloride is weighed in a 250-mL flask and 219.4 mL of ultra-pure water is added. The following are then added, in this order: 25 mL of the solution of HEPES prepared according to Example 3, 625 µL of the solution of europium prepared according to Example 1 and 5 mL of the solution of 2,5-diaminopyridine prepared according to Example 2.

Example 5

Preparation of a Stock Solution of Water-Soluble Anionic Polymer 3630

The water-soluble anionic polymer 3630 is a random copolymer of acrylamide and sodium acrylate (70/30 in mol %). It is a linear polymer having a molecular weight of about 18 MDa.

A 10 g/L concentrated solution of water-soluble anionic polymer 3630 in salt water is prepared by dissolving 1 g of polyacrylamide 3630 in 100 mL of salt water (referenced at 6 g/L). 1 mL of this solution is taken and is put in a 100-mL flask and 99 mL of salt water (referenced at 6 g/L) is added. A 100 ppm solution of water-soluble anionic polymer 3630 in salt water is obtained.

Example 6

Preparation of a Stock Solution of Water-Soluble Anionic Polymer AN977

The water-soluble anionic polymer AN977 is a random copolymer of acrylamide and sodium acrylate (34/66 in mol %). It is a linear polymer having a molecular weight of about 8 MDa.

A 100 ppm solution of water-soluble anionic polymer AN977 in salt water is prepared according to the procedure described in Example 5 using 1 g of polyacrylamide AN977 in place of 1 g of polyacrylamide 3630.

Example 7

Preparation of a Stock Solution of Water-Soluble Anionic Polymer AN125

The water-soluble anionic polymer AN125 is a random copolymer of acrylamide and acrylamido-2-methyl-2-propanesulphonic acid (75/25 in mol %). It is a linear polymer having a molecular weight of about 8 MDa.

A 100 ppm solution of water-soluble anionic polymer AN125 in salt water is prepared according to the procedure described in Example 5 using 1 g of polyacrylamide AN125 in place of 1 g of polyacrylamide 3630.

II—Detection and Quantification of the Polymers

Quantification of the Additives by Time-Resolved Fluorescence (TRF):

The measurements were carried out on an Agilent Cary Eclipse spectrofluorometer. The luminescence lifetime of the rare earths increases with the decrease in the number of water molecules in their coordination sphere. Complexing of the rare earths by the polymers thus allows them to be detected and quantified.

The fluorescence lifetimes of these complexes are typically of the order of a millisecond. This property in particular makes it possible to distinguish them from the fluorescence of organic compounds, which is of the order of a microsecond.

The complexes of europium have four notable emission peaks in the visible: 536, 595, 614 and 650 nm. The limits of the equipment (loss of sensitivity for $\lambda em > 650$ nm) led us to quantify these entities via the emission at 614 nm. The intensity of the peak is related to the concentration, the degree of complexing and the detection conditions.

Example 8

Quantification of Polymer 3630—Plotting a Calibration Line

A range of standard solutions 0-100 ppm is prepared by dilution with salt water at 6 g/L of the solution at 100 ppm prepared in Example 5. Each standard is then diluted 10-fold in the detecting solution prepared according to Example 4. For this, 9 mL of the detecting solution prepared according to Example 4 is taken and introduced into a 10-mL flask. 1 mL of the standard solution to be assayed is added. After 1 h, 2.5 mL of the mixture of standard and detecting solution is taken and introduced into a spectrophotometer tank (ref: Sarstedt® PMMA cuvette 2.5-4.5 mL). The contents of the cuvette are finally analysed by time-resolved fluorescence.

FIG. 1 shows the calibration line obtained. These data show that it is possible to carry out quantitative analyses of additives used in the enhanced recovery of oil and shale gas in an aqueous fluid.

Example 9

Quantification of Polymer AN977—Plotting a Calibration Line

A range of standard solutions 0-100 ppm is prepared by dilution in salt water at 6 g/L of the solution at 100 ppm prepared in Example 6. Each standard is then diluted 20-fold in the detecting solution prepared according to Example 4. For this, 9.5 mL of the detecting solution from Example 4 is taken and introduced into a 10-mL flask. 0.5 mL of the standard solution to be assayed is added. After 1 h, 2.5 mL of the mixture of standard and detecting solution is taken and introduced into a spectrophotometer tank (ref: Sarstedt® PMMA cuvette 2.5-4.5 mL). The contents of the cuvette are finally analysed by time-resolved fluorescence.

Figure 2:
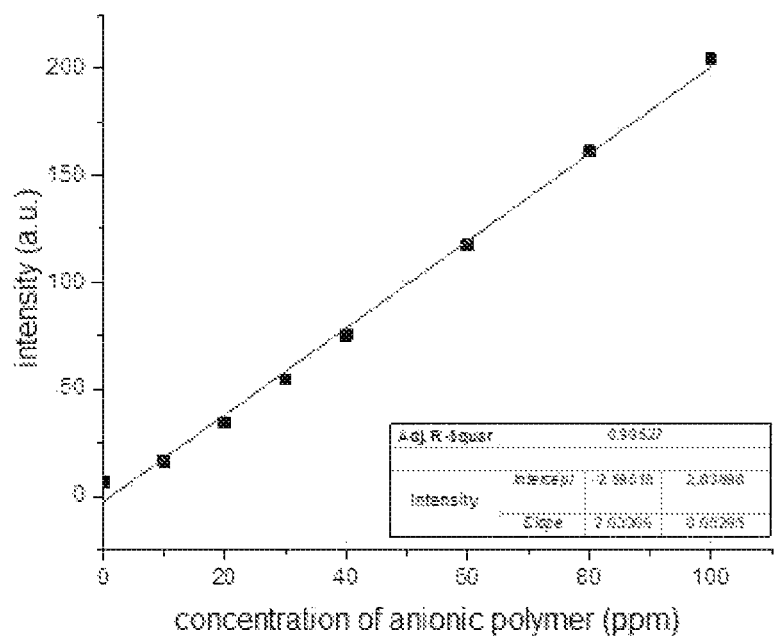
FIG. 2 shows the calibration curve of polymer AN977 with Eu-2,5-diaminopyridine according to Example 9.

FIG. 2 shows the calibration line obtained. These data show that it is possible to carry out quantitative analyses of additives used in the enhanced recovery of oil and shale gas in an aqueous fluid.

Example 10

Quantification of Polymer AN125—Plotting a Calibration Line

A range of standard solutions 0-60 ppm is prepared by dilution with salt water at 6 g/L of the solution at 100 ppm prepared in Example 7. Each standard is then diluted 5-fold in the detecting solution prepared according to Example 4. For this, 8 mL of the detecting solution from Example 4 is taken and introduced into a 10-mL flask. 2 mL of the standard solution to be assayed is added. After 1 h, 2.5 mL of the mixture of standard and detecting solution is taken and introduced into a spectrophotometer tank (ref: Sarstedt® PMMA cuvette 2.5-4.5 mL). The contents of the cuvette are finally analysed by time-resolved fluorescence.

Figure 3:
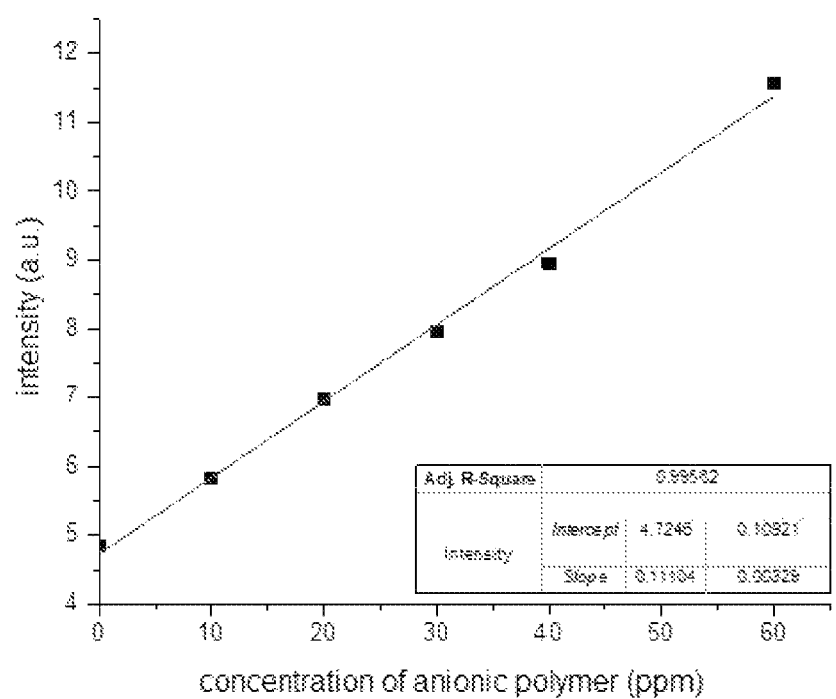
FIG. 3 shows the calibration curve of polymer AN125 with Eu-2,5-diaminopyridine according to Example 10.

FIG. 3 shows the calibration line obtained. These data show that it is possible to carry out quantitative analyses of additives used in the enhanced recovery of oil and shale gas in an aqueous fluid.

The invention claimed is:

1. A method for detecting additives used in the enhanced recovery of oil and shale gas, in injection water or production water, said method comprising:
   a. mixing a detecting solution comprising at least one lanthanide cation and optionally a chelating agent of the lanthanides, with a sample of injection water or of production water to be analysed comprising at least one additive used in the enhanced recovery of oil and shale gas, under conditions allowing complexing of the lanthanide by the additive present,
   b. detecting and, if appropriate, quantifying the variation in fluorescence associated with the presence of the additive in the injection water or the production water by time-resolved fluorescence,
   wherein the additive used in the enhanced recovery of oil and shale gas is a water-soluble polymer having a molecular weight between 1 MDa and 30 MDa.

2. The method according to claim 1, wherein the additive is selected from:
   polymers comprising at least one repeat unit comprising an amide bond;
   anionic biopolymers;
   cationic polymers.

3. The method according to claim 2, wherein the polymer comprising at least one repeat unit comprising an amide bond comprises a repeat unit of formula I

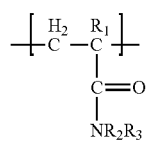

where $R_1$ is —H or —$CH_3$,
$R_2$ is —H or a substituted or unsubstituted $C_1$ to $C_4$ alkyl group,
$R_3$ is —H or a substituted or unsubstituted $C_1$ to $C_4$ alkyl group, or an -L-$R_4$ group,
where L is a bond or a substituted or unsubstituted $C_1$ to $C_{10}$ alkyl group, interrupted by 0, 1 or more —$NR_2$— or —O— or —S— bonds, or a -(substituted or unsubstituted $C_1$ to $C_{10}$ alkyl)-($N^+R_6R_7$)-(substituted or unsubstituted $C_1$ to $C_{10}$ alkyl)- group with $R_6$ and $R_7$ which are either —H or a substituted or unsubstituted $C_1$ to $C_4$ alkyl group,
and $R_4$ is —H or a carboxylate group (—$COO^-$) or a sulphonate group (—$SO_3^-$), or with optionally with a counter-ion.

4. The method according to claim 3, wherein the polymer moreover comprises a repeat unit of formula II

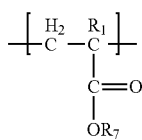

where $R_1$ is —H or —$CH_3$,
and $OR_7$ is O—H or $O^-$ and a counter-ion.

5. The method according to claim 3, wherein the polymer moreover comprises a repeat unit of formula III

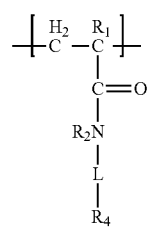

where $R_1$ is —H or —$CH_3$,
$R_2$ is —H or a substituted or unsubstituted $C_1$ to $C_4$ alkyl group,
L is a bond or a substituted or unsubstituted $C_1$ to $C_{10}$ alkyl group, interrupted by 0, 1 or more —$NR_2$— or —O— or —S— bonds, or a -(substituted or unsubstituted $C_1$ to $C_{10}$ alkyl)-($N^+R_6R_7$)-(substituted or unsubstituted $C_1$ to $C_{10}$ alkyl)- group with $R_6$ and $R_7$ which are either —H or a substituted or unsubstituted $C_1$ to $C_4$ alkyl group,
and $R_4$ is —H or a carboxylate group (—$COO^-$) or a sulphonate group (—$SO_3^-$), optionally with a counter-ion.

6. The method according to claim 3, wherein the polymer moreover comprises a repeat unit originating from the polymerization of a non-ionic monomer, the non-ionic monomer is selected from acryloyl morpholine, N-vinylcaprolactam, N-vinylpyrrolidone, N,N-dimethylacrylamide, N-ispropylacrylamide, diacetone acrylamide, N-vinylformamide, N-vinylacetamide, N-vinylpyridine, hydroxybutyl vinyl ether and isoprenol.

7. The method according to claim 3, wherein the polymer moreover comprises a repeat unit comprising a hydrophobic group, of formula IV

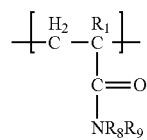

where $R_1$ is —H or —$CH_3$,
$R_8$ and $R_9$ are independently a substituted or unsubstituted $C_7$ to $C_{20}$ alkyl group, a substituted or unsubstituted aryl group, a substituted or unsubstituted -aryl-($C_1$ to $C_{20}$ alkyl) group or substituted or unsubstituted —($C_1$ to $C_{20}$ alkyl)-aryl group,
where $R_8$ and/or $R_9$ are different from H.

8. The method according to claim 1, wherein the detecting solution moreover comprises at least 1 g/L of chloride ions, and a concentration of chloride ions comprised between 5 and 50 g/L.

9. The method according to claim 1, wherein the detecting solution moreover comprises at least 1 g/L of a chemical compound used in the production of buffer solution, of 4-(2-hydroxyethyl)-1-piperazine-ethanesulphonic acid (HEPES) or sodium acetate.

10. The method according to claim 1, wherein the lanthanide is selected from: Pr, Nd, Sm, Eu, Tb, Dy, Ho, Er, Tm and Yb, as well as mixtures thereof.

11. The method according to claim 1, wherein the additive is present at a concentration less than or equal to 10 ppm in the sample of injection water or of production water to be analysed.

* * * * *